(12) United States Patent
Mainsah et al.

(10) Patent No.: US 11,931,562 B2
(45) Date of Patent: Mar. 19, 2024

(54) TECHNIQUES FOR IDENTIFYING ACOUSTIC BIOMARKERS IN LEFT VENTRICULAR ASSIST DEVICE RECIPIENTS

(71) Applicant: Duke University, Durham, NC (US)

(72) Inventors: Boyla Mainsah, Durham, NC (US); Priyesh Patel, Concord, NC (US); Leslie M. Collins, Chapel Hill, NC (US); Ravi Karra, Durham, NC (US); Emma LaPorte, Durham, NC (US); Xinlin Chen, Durham, NC (US)

(73) Assignee: Duke University, Durham, NC (US)

( * ) Notice: Subject to any disclaimer, the term of this patent is extended or adjusted under 35 U.S.C. 154(b) by 329 days.

(21) Appl. No.: 17/336,017

(22) Filed: Jun. 1, 2021

(65) Prior Publication Data
US 2021/0370045 A1    Dec. 2, 2021

Related U.S. Application Data

(60) Provisional application No. 63/046,305, filed on Jun. 30, 2020, provisional application No. 63/046,274, filed on Jun. 30, 2020, provisional application No. 63/033,489, filed on Jun. 2, 2020.

(51) Int. Cl.
| | | |
|---|---|---|
| A61M 60/00 | (2021.01) | |
| A61M 60/178 | (2021.01) | |
| A61M 60/216 | (2021.01) | |
| A61M 60/515 | (2021.01) | |
| A61M 60/538 | (2021.01) | |
| G10L 21/0232 | (2013.01) | |
| G10L 25/18 | (2013.01) | |
| G10L 25/21 | (2013.01) | |
| G10L 25/66 | (2013.01) | |
| G16H 40/67 | (2018.01) | |

(52) U.S. Cl.
CPC ........ A61M 60/515 (2021.01); A61M 60/178 (2021.01); A61M 60/216 (2021.01); A61M 60/538 (2021.01); G10L 21/0232 (2013.01); G10L 25/18 (2013.01); G10L 25/21 (2013.01); G10L 25/66 (2013.01); G16H 40/67 (2018.01); *A61M 2205/3365* (2013.01); *A61M 2205/3375* (2013.01); *A61M 2205/50* (2013.01); *A61M 2230/04* (2013.01)

(58) Field of Classification Search
CPC ................................. A61N 1/362; A61N 1/37
See application file for complete search history.

(56) References Cited

U.S. PATENT DOCUMENTS

2019/0184177 A1* 6/2019 Volpe ................. A61N 1/36578
2019/0298903 A1* 10/2019 Gillberg ............... A61B 5/6805

\* cited by examiner

*Primary Examiner* — Michael J D'Abreu
(74) *Attorney, Agent, or Firm* — Kory D. Christensen (57) ABSTRACT

Disclosed are systems and techniques for determining an acoustic biomarker. For example, a precordial sound recording that includes at least a first sound component corresponding to a heart and a second sound component corresponding to a left ventricular assist device (LVAD) can be obtained. At least a portion of the second sound component corresponding to the LVAD can be filtered from the precordial sound recording to yield a filtered precordial sound recording. Based on the filtered precordial sound recording, at least one acoustic biomarker can be determined.

22 Claims, 8 Drawing Sheets

TECHNIQUES FOR IDENTIFYING ACOUSTIC BIOMARKERS IN LEFT VENTRICULAR ASSIST DEVICE RECIPIENTS

CROSS-REFERENCE TO RELATED APPLICATIONS

This application claims the benefit of U.S. Provisional Application No. 63/033,489, filed Jun. 2, 2020, for "Signal Processing to Mitigate LVAD Sounds in LVAD Audio Recording," U.S. Provisional Application No. 63/046,305, filed Jun. 30, 2020, for "Acoustic Biomarker Method for Quality of Life in LVAD Recipients," and U.S. Provisional Application No. 63/046,274, filed Jun. 30, 2020, for "Signal Processing to Mitigate LVAD Sounds in LVAD Audio Recording," each of which is incorporated herein by reference.

BACKGROUND

Left ventricular assist devices (LVADs) are surgically implanted mechanical pumps that can be used to improve survival rates for individuals with advanced heart failure. LVAD recipients generally report an improved quality of life (QoL) following LVAD implantation. However, LVAD therapy is also associated with high morbidity, which can be partially attributed to the difficulties in identifying an LVAD complication before an adverse event occurs.

Methods that are currently used to monitor for complications in LVAD-supported individuals require frequent clinical assessments at specialized LVAD centers. Moreover, assessing the health of an LVAD patient's heart is challenging because of the noise caused by the mechanical pump as well as the effect on the cardiac cycle. Hence, there is a need for an improved diagnostic tool that can facilitate point of care as well as remote monitoring for early detection of complications.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

One aspect of the present disclosure provides a method of determining an acoustic biomarker, the method includes: obtaining a precordial sound recording including at least a first sound component corresponding to a heart and a second sound component corresponding to a left ventricular assist device (LVAD); filtering at least a portion of the second sound component corresponding to the LVAD from the precordial sound recording to yield a filtered precordial sound recording; and determining, based on the filtered precordial sound recording, at least one acoustic biomarker.

Another aspect of the present disclosure provides an apparatus for determining an acoustic biomarker. The apparatus comprises at least one memory, at least one transducer, and at least one processor coupled to the at least one memory and the at least one transducer. The at least one processor is configured to: obtain, via the at least one transducer, a precordial sound recording including at least a first sound component corresponding to a heart and a second sound component corresponding to a left ventricular assist device (LVAD); filter at least a portion of the second sound component corresponding to the LVAD from the precordial sound recording to yield a filtered precordial sound recording; and determine, based on the filtered precordial sound recording, at least one acoustic biomarker.

Another aspect of the present disclosure may include a non-transitory computer-readable storage medium having stored thereon instructions which, when executed by one or more processors, cause the one or more processors to: obtain a precordial sound recording including at least a first sound component corresponding to a heart and a second sound component corresponding to a left ventricular assist device (LVAD); filter at least a portion of the second sound component corresponding to the LVAD from the precordial sound recording to yield a filtered precordial sound recording; and determine, based on the filtered precordial sound recording, at least one acoustic biomarker Another aspect of the present disclosure may include an apparatus for determining an acoustic biomarker. The apparatus includes: means for obtaining a precordial sound recording including at least a first sound component corresponding to a heart and a second sound component corresponding to a left ventricular assist device (LVAD); means for filtering at least a portion of the second sound component corresponding to the LVAD from the precordial sound recording to yield a filtered precordial sound recording; and means for determining, based on the filtered precordial sound recording, at least one acoustic biomarker.

These and other aspects will be described more fully with reference to the Figures and Examples disclosed herein.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments.

DETAILED DESCRIPTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs.

Left ventricular assist devices (LVADs) are surgically implanted pumps that can be used to improve the survival rate of patients with advanced heart failure. An LVAD can assist heart function by rerouting blood from the left ventricle of the heart into the aorta via a mechanical pump. While conferring a survival benefit, LVAD therapy is also characterized by a high complication rate and is associated with significant hospital readmission rates. Common complications include infection, gastrointestinal bleeding, right heart failure, stroke, and formation of blood clots within the LVAD (or thrombosis).

Due to the high complication rate associated with LVAD therapy, the clinical management of LVAD-supported individuals involves routine clinic visits to assess patient health. Despite this, many LVAD complications are not detected until they are at an advanced stage, when patients present with severe or life-threatening symptoms, resulting in prolonged hospital stays and the need to pursue high risk rescue strategies.

Frequent visits to specialized LVAD centers can be costly. Furthermore, assessing the health of an LVAD patient's heart using traditional auscultation techniques (e.g., listening to heart with stethoscope) is challenging because pump sounds obscure intrinsic cardiac sounds. Without overt evidence for device malfunction, impending complications may not be readily apparent.

The present disclosure addresses these and other challenges by providing systems and techniques that can be used to enhance intrinsic sounds and determine acoustic biomarkers that are associated with improved quality of life (QoL) for LVAD patients. The present disclosure also provides systems and techniques that can be implemented remotely, which can diminish the need for regular visits to LVAD centers and can facilitate early detection of LVAD related complications through patient self-monitoring and/or via remote consultation with medical personnel (e.g., telemedicine).

One aspect of the present disclosure provides a system for determining an acoustic biomarker. The system comprises an audio recording device such as a digital stethoscope or any other type of device having a transducer (e.g., microphone) that is capable of capturing and/or recording precordial sounds. In some examples, the system can also include an audio processing device (e.g., digital signal processor) that is configured to process the precordial sound recording in order to filter audio components associated with the LVAD and identify one or more acoustic features (e.g., acoustic biomarker). In other embodiments, the audio recording device can send (e.g., via a network interface) the precordial sound recording to a computer, server, or any other computing device that can be configured to perform audio processing.

In some embodiments, acoustic features can be used to determine metrics associated with the quality of life of a left ventricular assist device (LVAD) recipient. In some cases, acoustic features can be used to identify LVAD related issues and/or determine adjustments to LVAD operating parameters. In some aspects, acoustic features can provide an indication and/or warning of a potential clinical event associated with the LVAD.

In some embodiments, the system includes an optional display device to report the results of the acoustic monitoring test. The report can be provided in any suitable format and include any representation of the data. Some example formats include a visual and/or graphical representation of the sound wave with an identification of one or more acoustic features. In some aspects, the display could include an electronic device such as a mobile device, tablet, laptop, smartwatch, and/or any other type of electronic device having a graphical user interface.

Figure 1:
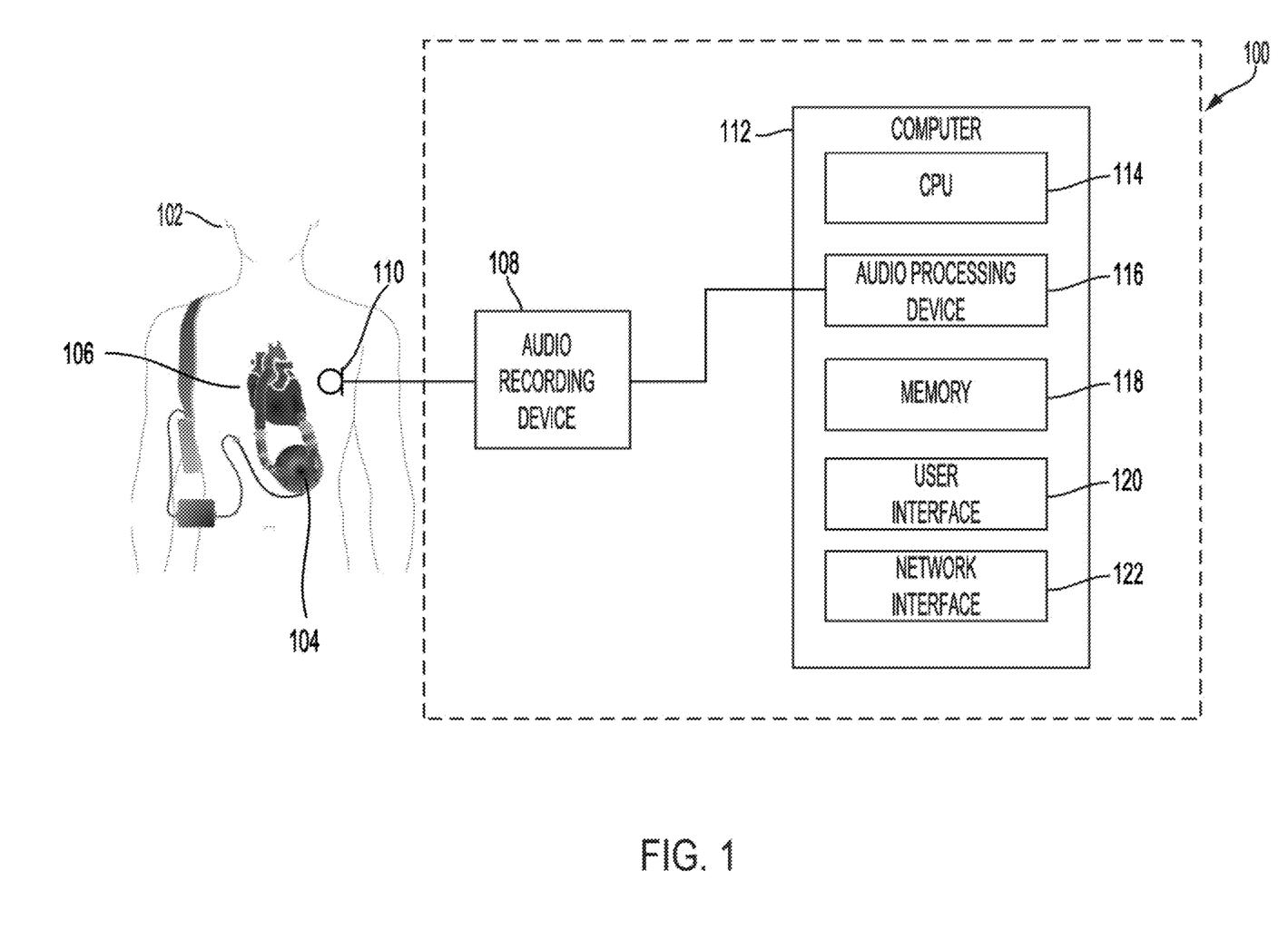
FIG. 1 is a schematic diagram of an acoustic biomarker detection system.

FIG. 1 is a schematic diagram of an acoustic biomarker detection system 100 according to one embodiment of the present disclosure. In some aspects, the acoustic biomarker detection system 100 can be used to record and analyze precordial sounds (e.g., sounds through the chest wall overlaying the heart) from a patient 102 having a left ventricle assist device (LVAD) 104 that is surgically implanted and assists functions of heart 106. Examples of LVAD 104 can include a HEARTMATE3™ (HM3) LVAD, a HEARTMATE II™ LVAD, a HEARTWARE HVAD™, or any other type of surgically implanted mechanical heart pump.

In some embodiments, acoustic biomarker detection system 100 can include an audio recording device 108 that is coupled to a transducer 110 (e.g., microphone). In some aspects, audio recording device 108 can be configured to capture, record, log, and/or store precordial sounds from patient 102. In some examples, audio recording device 108 can include a digital stethoscope. In other embodiments, audio recording device 108 can include any electronic device that can be configured to record audio such as a smartphone, tablet, laptop, desktop, smartwatch, etc. Audio recording device 108 may be connected to transducer 110 via a wired or a wireless transmission medium (e.g., BLUETOOTH™, Wi-Fi, Infrared, NFC, etc.).

In some configurations, acoustic biomarker detection system 100 can include a computer 112 (e.g., computing device) having one or more different components. In some cases, the computer 112 may be controlled by a central processing unit (CPU) 114, such as a microprocessor, although other types of controllers or processing devices may be used, such as a microcontroller, digital signal processor (DSP), application specific integrated circuit (ASIC), field-programmable gate array (FPGA) or like device. The CPU 114 may execute instructions stored in a memory 118, which may be implemented using any suitable non-transitory computer-readable medium, such as random access memory (RAM), read-only memory (ROM), electronically erasable programmable read-only memory (EEPROM), or the like. In some examples, memory 118 can also include non-volatile memory such as a hard disk drive (HDD), solid-state drive (SSD), and/or or optical storage unit, for long-term storage of data and/or application programs. The memory 118 may be local to the computer 112, as shown, or could be implemented remotely in the cloud.

The acoustic biomarker detection system 100 may include an audio processing device 116 for processing and aggregating data received from audio recording device 108. In various embodiments, the audio processing device 116 may be a component of the audio recording device 108, a standalone component, or, as illustrated, a hardware and/or software component of a computer 112 (e.g., a digital signal processor). As described more fully below, the audio processing device 116 may be used to process (e.g., sample, filter, encode, segment, etc.) precordial sounds received from audio recording device 108. In some examples, audio processing device 116 can process sound recordings that are stored on a memory (e.g., memory 118) and/or it can process a stream of audio received from audio recording device 108. The audio processing device 116 can be configured to implement one or more algorithms for filtering (e.g., band-pass filter, high-pass filter, low-pass filter, notch filter, adaptive filter, etc.), sampling, segmentation, power spectral density estimation, and/or a variety of other functions/algorithms to implement the processes and features described herein.

The audio processing device 116 may be connected via a wired or wireless connection to the audio recording device 108. Optionally, the audio processing device 116 may be coupled to a transducer 110, including, without limitation, a microphone that captures precordial audio signals from patient 102. Although the audio recording device 108, transducer 110, and audio processing device 116 are illustrated as separate components, those skilled in the art may will recognize that the devices may be combined in various embodiments.

In some embodiments, computer 112 may further include a user interface 120. User interface 120 can include any input and/or output mechanism that enables user interaction with computer 112. For example, user interface 120 can include a microphone for speech, a touch-sensitive screen for gesture or graphical input, a keyboard, a mouse, speakers, motion input, speech and so forth.

The computer 112 may further include a network interface 122 for connecting the computer 112 to a network (not illustrated), such as a local area network (LAN) and/or wide area network (WAN), including the Internet. The network interface 122 may implement any suitable network protocols using a wireless or wired transmission medium.

Furthermore, the various components described above with respect to acoustic biomarker detection system 100 may be implemented in separate devices, local or remote, that work in concert to perform the operations disclosed herein.

Figure 2:
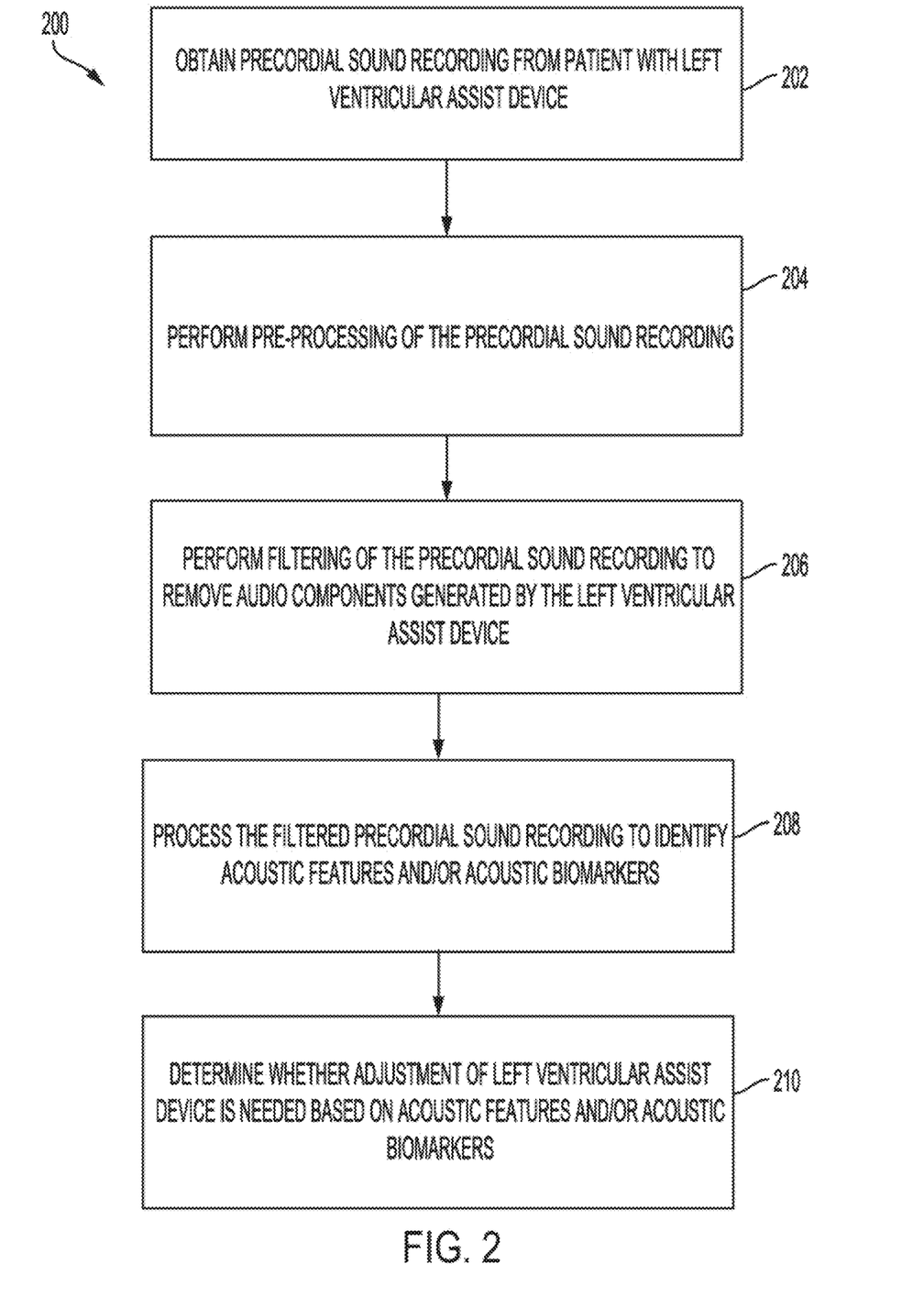
FIG. 2 is a flowchart illustrating an example method for determining an acoustic biomarker.

FIG. 2 illustrates an example of a method 200 for determining an acoustic biomarker. In some aspects, the operations of method 200 can be implemented by one or more computing devices that can be configured to capture, store, and process precordial sounds from a patient with a left ventricular assist device (LVAD), such as acoustic biomarker detection system 100.

At block 202, method 200 includes obtaining a precordial sound recording from a patient with an LVAD. In some embodiments, the precordial sound recording can be obtained using an audio recording device that is coupled to a transducer (e.g., a digital stethoscope). In some configurations, the sampling rate used to record the precordial sounds can be a frequency that is between 40 kiloHertz (kHz) and 50 kHz (e.g., 44.1 kHz or 48 kHz).

At block 204, method 200 includes performing pre-processing of the precordial sound recording. In some aspects, pre-processing can include implementing a band-pass filter with a frequency range corresponding to the expected frequency range of heart sounds. For instance, a band-pass filter from 20 Hertz (Hz) to 500 Hz can be used to restrict the range of frequencies to the expected range of normal and/or abnormal heart sounds. In some examples, the band-pass filter can have a smaller range (e.g., 20 Hz to 300 Hz). In some embodiments, pre-processing the precordial sound recording can also include resampling and/or down-sampling the sound recording. In one embodiment signals can be resampled using a frequency that is between 600 Hz and 1 kHz.

At block 206, method 200 includes filtering of the precordial sound recording to remove audio components generated by the left ventricular assist device. In some cases, filtering the precordial sound recording to remove audio components generated by the LVAD can include determining the frequency spectrum generated by an LVAD, which is dependent upon the pump's rotational speed. For instance, the frequency spectrum of LVAD-generated sounds can be characterized by peaks at multiples, or harmonics, of the pump's fundamental frequency, $f$. The fundamental frequency of the pump, expressed in Hz, is determined accordingly:

$$f = r/60, \qquad (1)$$

where r corresponds to the pump's rotational speed in revolutions per minute (rpm). In addition, the frequency spectrum can include frequency peaks at multiples of the fundamental frequency. Key harmonics occur at multiples of the blade passing frequency, which can be determined as follows:

$$f_{bp} = b \times f \qquad (2)$$

where $f_{bp}$ refers to the blade-passing frequency; b refers to the number of impeller blades or blood flow channels in the LVAD rotor; and $f$ refers to the pump's fundamental frequency.

In some aspects, an adaptive filter with a noise cancellation architecture can be used to isolate LVAD noise from the precordial sound recording. For example, to estimate the noisy signal component (n) within a signal mixture (s+n), a noise reference signal ($n_{ref}$) that is correlated with the noise within the mixture and uncorrelated with the signal(s) of interest can be used. The noise estimate ñ can be subtracted from the signal mixture to obtain a de-noised signal, ŝ=(s+n)−ñ. In some embodiments, a closed-loop process can be used in which the filter weights are adapted iteratively to minimize the signal difference. A normalized least-mean-squares (nLMS) adaptive filter can be used, with the filter weights updated as follows:

$$w(t+1) = w(t) + \frac{\overline{\mu}}{\varepsilon + n_{ref}^T(t) n_{ref}(t)} \epsilon(t) n_{ref}(t) \qquad (3)$$

In equation (3), w corresponds to the titter weight vector; t is the current time index; $\overline{\mu}$ is the nominal step size; $n_{ref}$ is the noise reference; $\epsilon$=(s+n)−ñ refers to the difference between the filter output and the mixture of signals; and ε is a small constant that can be used to prevent division by a very small number.

In some aspects, the input signal mixture corresponds to the recording of precordial sounds, the noise within the mixture corresponds to the LVAD-generated sounds, and the output after adaptive filtering corresponds to the intrinsic precordial sounds (e.g., a de-noised phonocardiogram (PCG) signal). In some embodiments, a noise reference can be generated with a mixture of sinusoids corresponding to the frequencies at the LVAD harmonics of interest falling below 500 Hz, as determined by equations (1) and (2). In some cases, an nLMS filter with a fixed sample length (e.g., 200 samples) can be implemented using a filter step size $\overline{\mu}$ that can be tuned by assessing the attenuation of amplitudes at LVAD-specific frequencies in the de-noised signal.

In one illustrative example, an LVAD such as the HM3 can undergo a periodic speed change/oscillation (e.g., every 2 seconds) to wash the impeller. For instance, the speed change can cause the pump's speed to decrease to 2000 rpm for 0.15 s, increase to 4000 rpm for 0.2 s, then return to primary (programmed) speed. In some cases, the speed oscillation can result in an "artificial pulse" and can generate sounds with short bursts of energy at secondary frequencies. As noted above, such noise can be filtered using noise reference signals that can be generated using sinusoids at frequencies corresponding to harmonics of the pump's fundamental frequency. In the case of the HM3 LVAD, adaptive filtering can be modified to target (e.g., filter, cancel, etc.) primary and secondary pump frequencies using separate noise references.

Figure 3A:
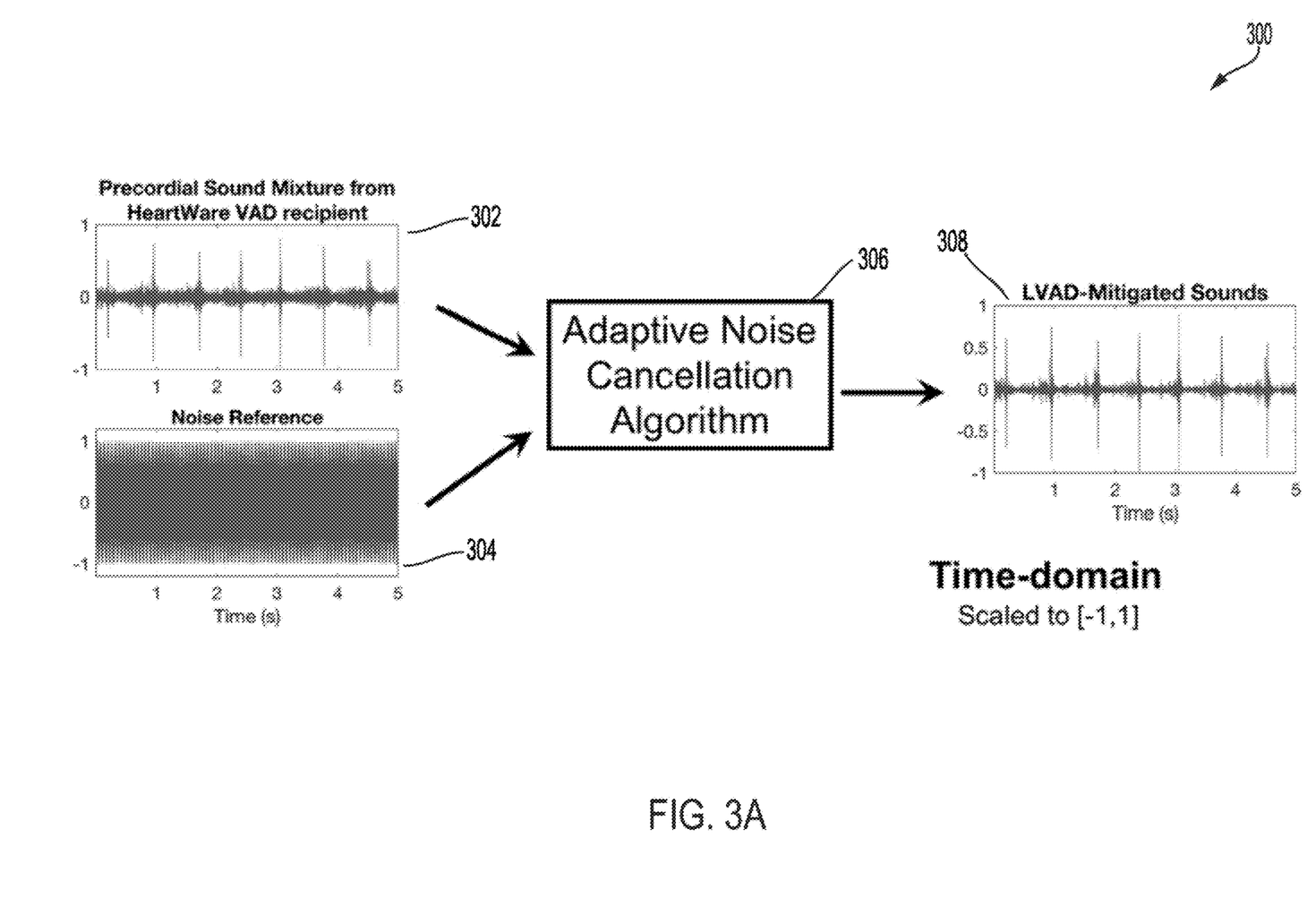
FIG. 3A and FIG. 3B are graphical representations of adaptive filtering techniques.

FIG. 3A illustrates an example of adaptive filtering 300 that can be performed to isolate LVAD noise from the precordial sound recording. As noted above, adaptive filtering (e.g., noise cancellation algorithm 306) can receive as input a precordial sound mixture 302 (e.g., from LVAD recipient) and noise reference 304 corresponding to the LVAD generated sounds (e.g., based on LVAD parameters). The output of adaptive noise cancellation algorithm 306 corresponds to LVAD-mitigated sounds 308, as illustrated in the time domain.

Figure 3B:
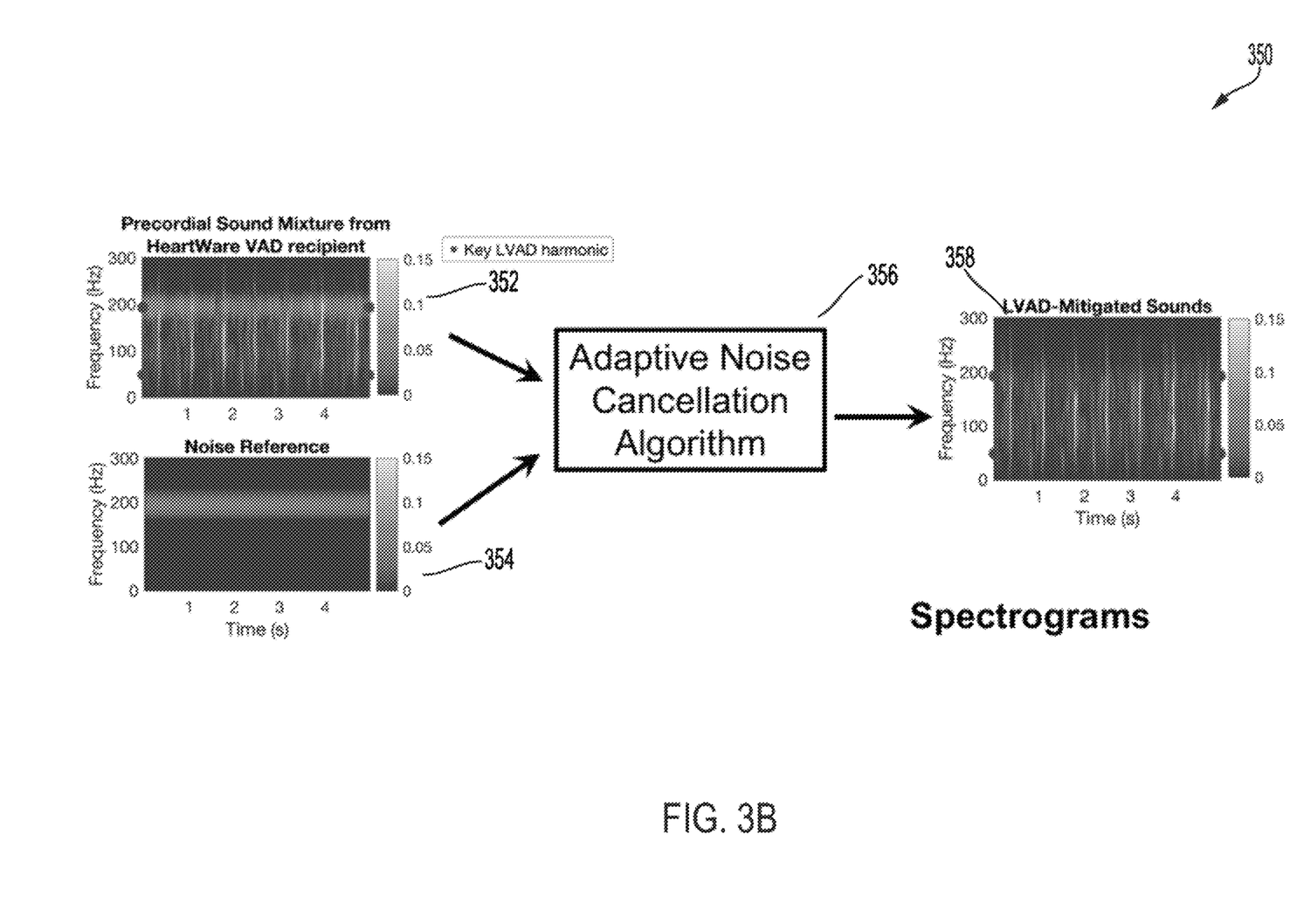

FIG. 3B illustrates another example of adaptive filtering 350 that can be performed to isolate LVAD noise from the precordial sound recording. Adaptive filtering can be implemented using adaptive noise cancellation algorithm 356, which can receive as input a precordial sound mixture 352 (e.g., from LVAD recipient) and noise reference 354 corresponding to the LVAD generated sounds (e.g., based on LVAD parameters). The output of adaptive noise cancellation algorithm 356 corresponds to LVAD-mitigated sounds 358, as illustrated in the frequency domain.

Returning to FIG. 2, at block 208 the method 200 includes processing the filtered precordial sound recording to identify acoustic features and/or acoustic biomarkers and to enhance intrinsic sounds. In one embodiment, an automatic heart sound segmentation algorithm can be used to segment the filtered precordial sound recording (e.g., de-noised phonocardiogram signal) into four stages of a cardiac cycle, which include: (1) the first heart sound or S1 (closure of atrioventricular valves); (2) systole (heart muscle contraction); (3) the second heart sound or S2 (closure of semi-lunar valves); and (4) diastole (heart muscle relaxation). In some aspects, S1 and S2 can be referred to as the fundamental heart sounds (FHSs), and systole and diastole can be referred to as the inter-FHS regions. In general, the FHSs are the loudest sounds occurring in a PCG signal, and exhibit distinct frequency characteristics. The majority of the energy in S1 and S2 is concentrated below 150 Hz, with S2 having frequency range (e.g., 24-144 Hz) that is wider than the frequency range for S1 (e.g., 24-104 Hz). In some cases, the inter-FHS regions may contain extra heart sounds (S3 and S4) and murmurs (due to stenosis, regurgitation, etc.) that may be indicative of additional pathology.

In one aspect, heart sound segmentation can be implemented using one or more heart sound segmentation algorithms. In one illustrative example, an algorithm that is based on a hidden semi-Markov model (HSMM) that incorporates expected stage durations and logistic regression-based emission probabilities can be used to determine the most likely sequence of stages. In one example, the input features can include: the homomorphic envelogram; the Hilbert envelope; the wavelet envelope; and the power spectral density (PSD) envelope, which can be calculated at a sampling frequency of 50 Hz. In some cases, the parameters of the HSMM can be trained using a database of PCG signals collected from a non-LVAD population.

In some embodiments, the output of the sound segmentation algorithm can be further processed and/or analyzed using one or more techniques. In one example, post-segmentation analysis can be performed by averaging extracted features over each segmented cycle stage and reducing the dimensionality of the averaged features by using principal component analysis (PCA).

In another example, post-segmentation analysis can be performed by comparing similarities of signals within the same stage and between stages. For example, S1 and S2 sounds are expected to be more similar to each other than to any other stage, and to be more similar to each other than to the generally quieter inter-FHS regions. For instance, the cross-correlation metric can be used to measure the similarity between two signals as a function of the delay of one relative to the other, as follows:

$$R_{x,y}[l] = E\{x[t]y^*[t-l]\} \qquad (4)$$

In equation (4), $R_{x,y}[l]$ denotes the cross-correlation between two signals, x and y, at a lag l of one signal relative to the other; t is the time index; * denotes the complex conjugate of a signal; and E{ } denotes the expected value. The cross-correlation metric accounts for non-alignment and amplitude scale differences (via a normalized measure) between signal pairs. The maximum cross-correlation between two signals ($R_{x,y}^{max}$) across times lags can be determined for each signal pair. The average maximum within-stage and between-stage cross-correlations can be computed based on pairings of signals of the same stage and across two stages, respectively.

In another example, post-segmentation analysis can be performed using power spectral density estimation. For example, frequency representations of the signals can be used to assess the removal of LVAD harmonics of interest after adaptive filtering and to compare the frequency characteristics of the segmented signals with expected heart sound characteristics. A periodogram can be used to estimate the power spectral density (PSD) of a signal against frequency, as follows:

$$\hat{P}_x(e^{j\omega}) = \frac{1}{N}|X(e^{j\omega})|^2. \qquad (5)$$

In equation (5), ω is the angular frequency; $\hat{P}_x(e^{j\omega})$ is the power spectral density estimate; $X(e^{j\omega})$ is the Fourier transform of the signal; and N is the signal length in samples.

In some embodiments, Welch's windowing and averaging method, which reduces the variance of the estimated PSD, can be used to compute the PSD estimates. Further, a Hann function can be used for windowing signals using different window lengths. For example, when the entire PCG signal is processed, a window length of 0.2 s and window overlap of 50% can be used to deliver an appropriate frequency resolution. Alternatively, when individual cardiac cycle stages are processed, a window length of 75% of the signal length (e.g., based on the small overall signal length) and an overlap of 50% can be used.

In another example, post-segmentation analysis can be performed using a short time Fourier transform or a continuous wavelet transform. For example, time-frequency representations of the de-noised PCG signals can be used to describe changes in the signals' frequency content over time, enabling comparisons between the characteristics of these signals and known characteristics of heart sounds. A one-dimensional (1-D) continuous wavelet transform (CWT) can be performed with the transform calculated accordingly:

$$\gamma(s,\tau) = \int f(t)\psi_{s,\tau}^*(t)dt \qquad (6)$$

Figure 4:
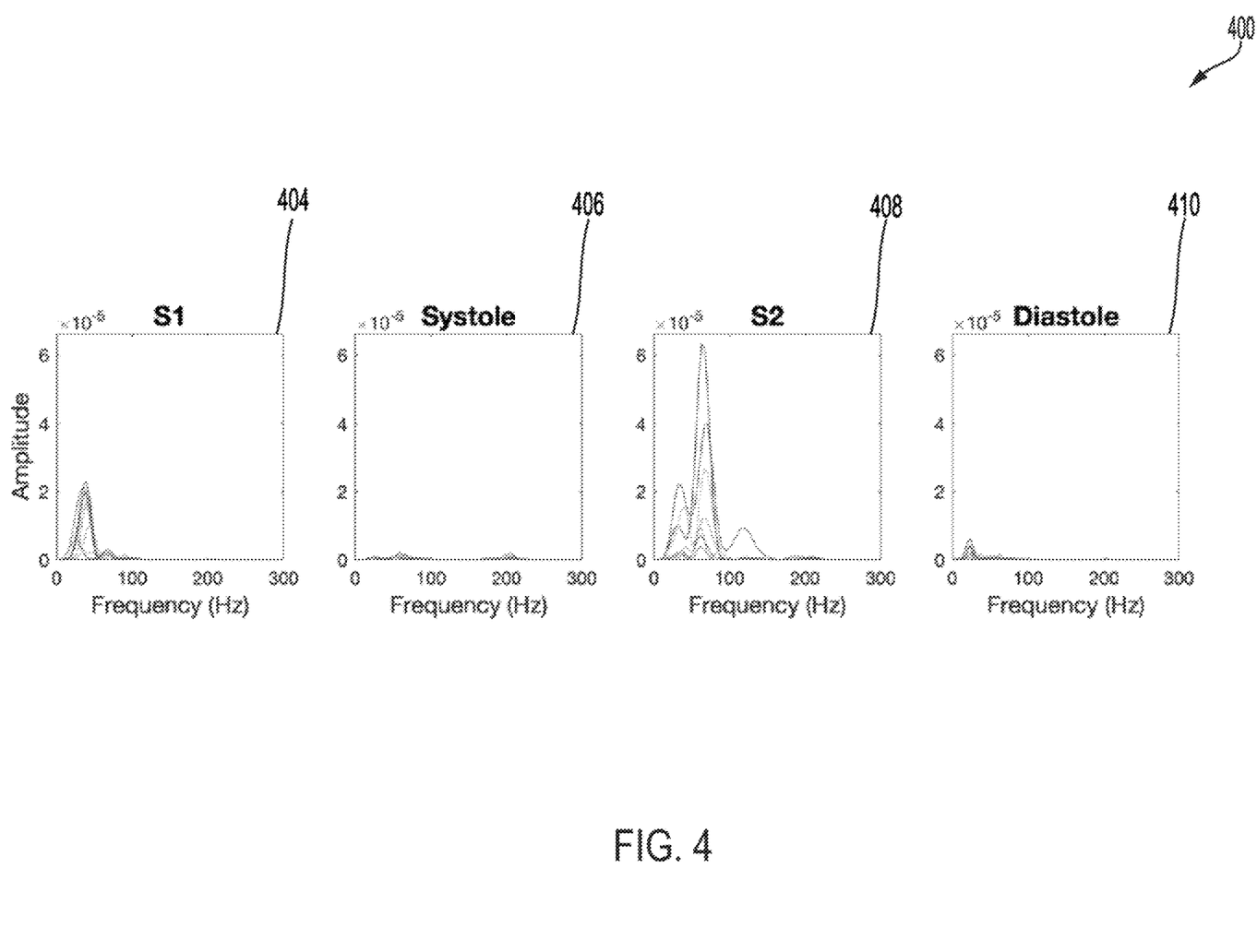
FIG. 4 is a graphical representation of power spectral density estimates of automatically extracted cardiac cycle stage segments.

In equation (6), γ(s, τ) is the continuous wavelet transform; ƒ(t) is the original signal that is decomposed into a set of basis functions s; ψ(t) generated from a mother wavelet; * denotes the complex conjugate; and s and τ denote the scaling and translation of the mother wavelet, respectively. In some cases, the Morlet wavelet can be used due to its similarity to the fundamental heart sounds and its ability to provide a reliable time-frequency representation for PCG signal analysis FIG. 4 illustrates an example of power spectral density estimates of the cardiac cycle stage segments 400 that were extracted from the filtered precordial sounds of an LVAD recipient. In some aspects, extracted cardiac cycle segments or data (e.g., S1, S2, etc.) can correspond to an acoustic biomarker. As illustrated, graph 404 corresponds to the first heart sound or S1 (closure of atrioventricular valves); graph 406 corresponds to systole (heart muscle contraction); graph 408 corresponds to the second heart sound or S2 (closure of semi-lunar valves); and graph 410 corresponds to diastole (heart muscle relaxation).

Returning to FIG. 2, in some examples, processing the filtered precordial sound recording to identify acoustic features and/or acoustic biomarkers (block 208) can include identifying an acoustic biomarker corresponding to a pulse synchronized sound (PSS) associated with an LVAD configured to perform speed oscillation. In some embodiments, the PSS can occur in the 20-100 Hz range and can include three transient energy bursts having a bandwidth that is wider than sounds associated with the pump (e.g., FIG. 5A and FIG. 5B). In some cases, the PSS acoustic biomarker can be associated with a higher than average quality of life for a patient and can reflect a favorable configuration of the LVAD (e.g., favorable degree of ventricular unloading and/or remodeling such that speed oscillations reverberate through the myocardium or vasculature). In some embodiments, identification of acoustic features (e.g., PSS acoustic biomarker) can be implemented using a Uniform Manifold Approximation and Projection (UMAP) algorithm. For instance, the acoustic features can correspond to normalized power spectral densities with a particular frequency range (e.g., 20-300 Hz), and can be estimated using Welch's method based on recording segments (e.g., 5 second segments).

Figure 5A:
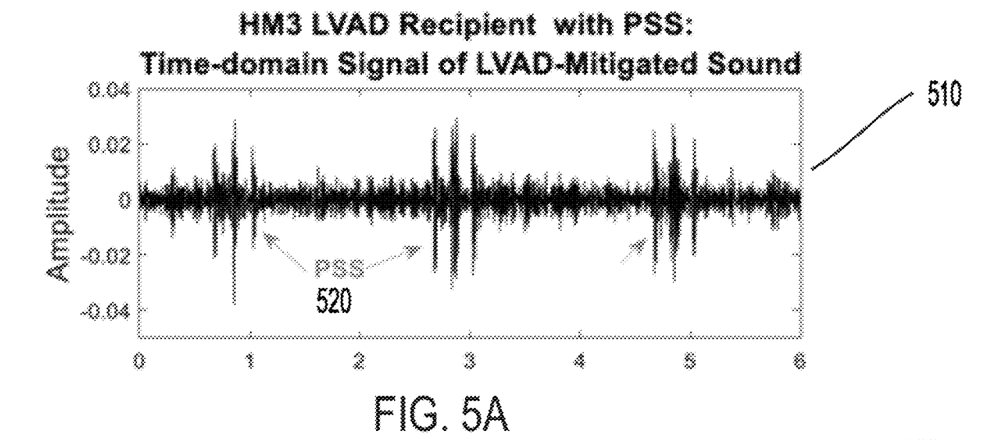
FIG. 5A illustrates a time-domain representation of a filtered precordial sound recording.
Figure 5B:
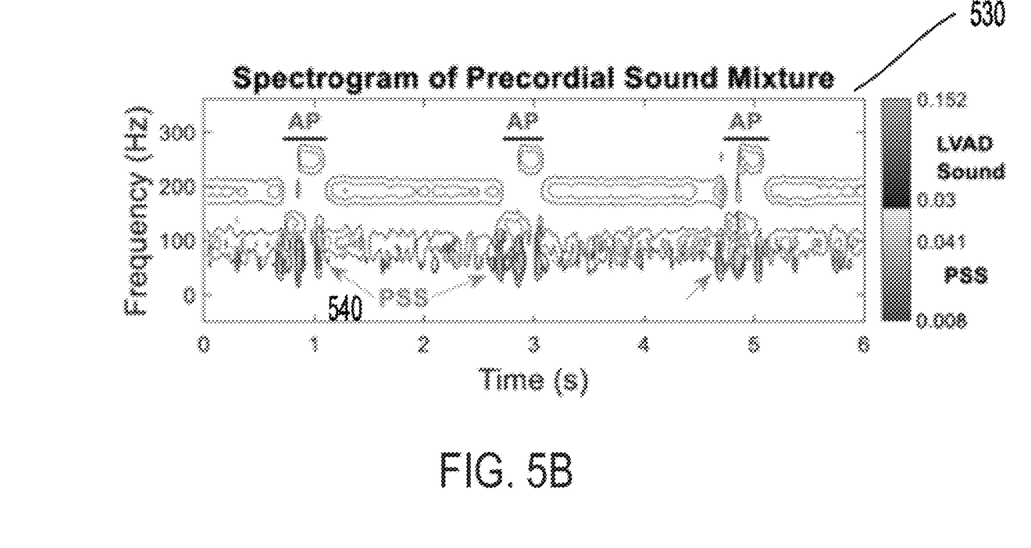
FIG. 5B illustrates a time-frequency representation of a precordial sound mixture.

FIG. 5A illustrates a time-domain representation 510 of a filtered precordial sound recording (e.g., LVAD mitigated sound) that includes the PSS acoustic biomarker 520. FIG. 5B illustrates a frequency domain representation 530 of a precordial sound mixture (e.g., spectrogram of LVAD sound combined with spectrogram of LVAD mitigated sound). In FIG. 5B, the PSS acoustic biomarker 540 is identified as part of the LVAD mitigated spectrogram (e.g., filtered precordial sound recording).

In some aspects, identification of an acoustic biomarker (e.g., PSS acoustic biomarker 520) can include and/or be implemented using artificial intelligence or machine learning algorithms. In one embodiment, a support-vector machine classifier can be used to detect the presence of the PSS acoustic biomarker. For example, the classifier can be trained with leave-one-subject out cross-validation.

At block 210, method 200 includes determining whether adjustment of LVAD is needed based on acoustic features and/or acoustic biomarkers. For example, the PSS acoustic biomarker, one or more extracted cardiac cycle segments (e.g., S1, S2, S3, S4), any other acoustic feature/biomarker, and/or any combination thereof can be used to determine changes or adjustments to LVAD. In one embodiment, the absence of an acoustic biomarker (e.g., PSS acoustic biomarker) can provide an indication of an adjustment to the LVAD. For example, the speed of the LVAD pump can be tuned in response to the detected presence and/or absence of an acoustic biomarker. In some aspects, the method 200 can be repeated after the LVAD pump is tuned in order to identify any changes associated with one or more acoustic biomarkers.

Figure 6:
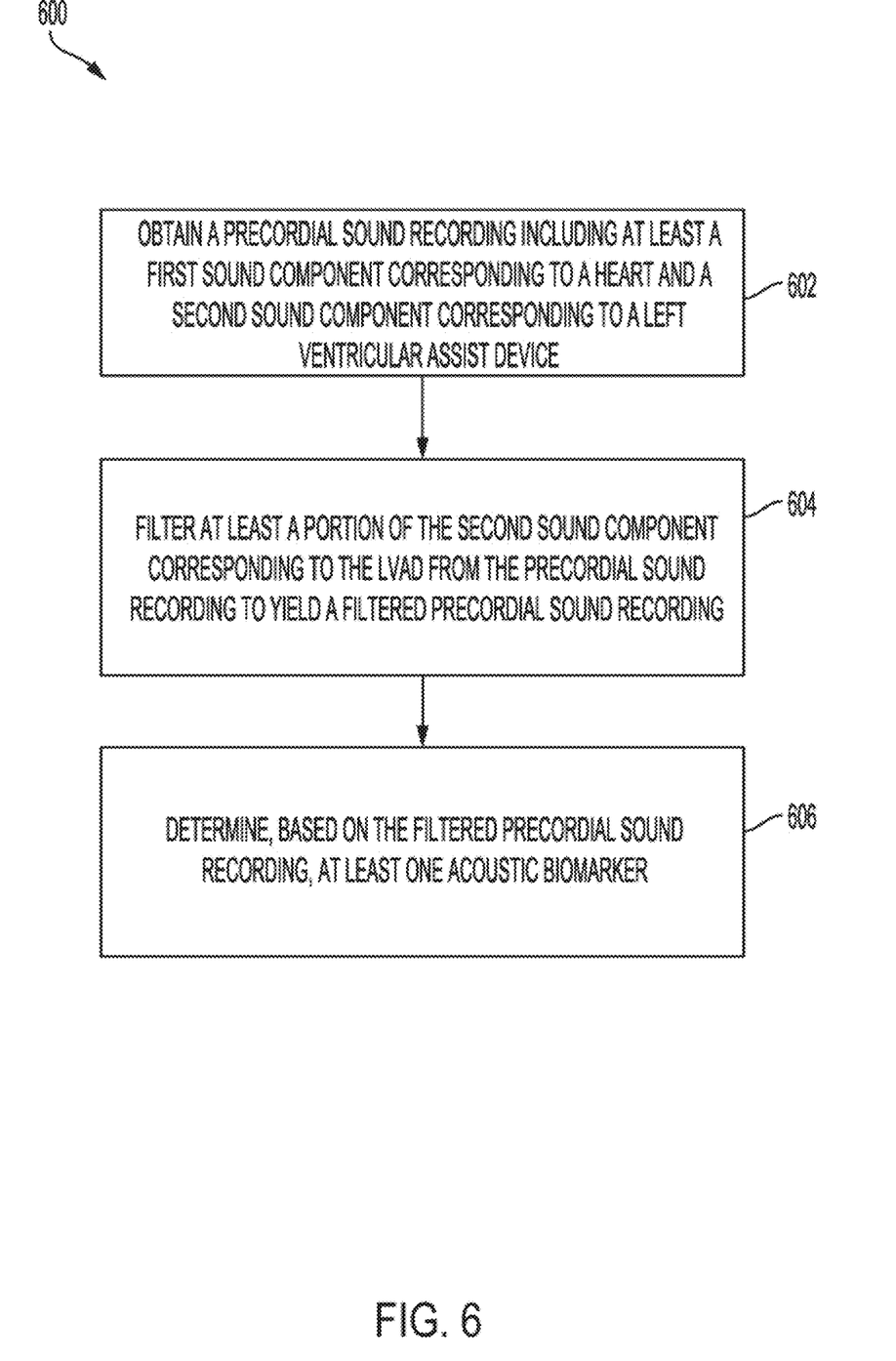
FIG. 6 is a flowchart illustrating another example method for determining an acoustic biomarker.

FIG. 6 illustrates and example method 600 for determining an acoustic biomarker. At block 602, the method 600 includes obtaining a precordial sound recording including at least a first sound component corresponding to a heart and a second sound component corresponding to a left ventricular assist device. For example, audio recording device 108 can obtain a precordial sound recording (e.g., using transducer 110) from patient 102. The recording can include a first sound component corresponding to heart 106 and a second sound component corresponding to LVAD 104. In some aspects, obtaining the precordial sound recording can include processing the precordial sound recording with a band-pass filter and reducing a sampling rate of the precordial sound recording (e.g., downsampling).

At block 604, the method 600 includes filtering at least a portion of the second sound component corresponding to the LVAD from the precordial sound recording to yield a filtered precordial sound recording. In some examples, the filtering can be implemented by a digital signal processor (e.g., CPU 114 or audio processing device 116). In some cases, the filtering can correspond to an adaptive noise cancelling algorithm, as illustrated in connection with FIG. 3A and FIG. 3B. In some aspects, the method can include determining, based on a rotational speed and a number of impeller blades, a frequency spectrum corresponding to the LVAD, wherein filtering the portion of the second sound component comprises filtering the frequency spectrum corresponding to the LVAD.

At block 606, the method 600 includes determining, based on the filtered precordial sound recording, at least one acoustic biomarker. In some examples, the at least one acoustic biomarker comprises one or more peaks in an amplitude of the filtered precordial sound recording (e.g., PSS acoustic biomarker 520). In some cases, the one or more peaks in the amplitude can correspond to a periodic speed oscillation of the LVAD.

In some embodiments, determining the at least one biomarker can comprise determining a normalized power spectral density within a range of 20 Hz to 300 Hz. In some aspects, the method can include processing the filtered precordial sound recording to identify one or more stages of a cardiac cycle. The one or more stages of the cardiac cycle can be identified based on a segmentation algorithm, as illustrated with respect to FIG. 4. In some examples, the method can include identifying an adjustment of a rotational speed of the LVAD in response to determining that the at least one acoustic biomarker is not present.

Figure 7:
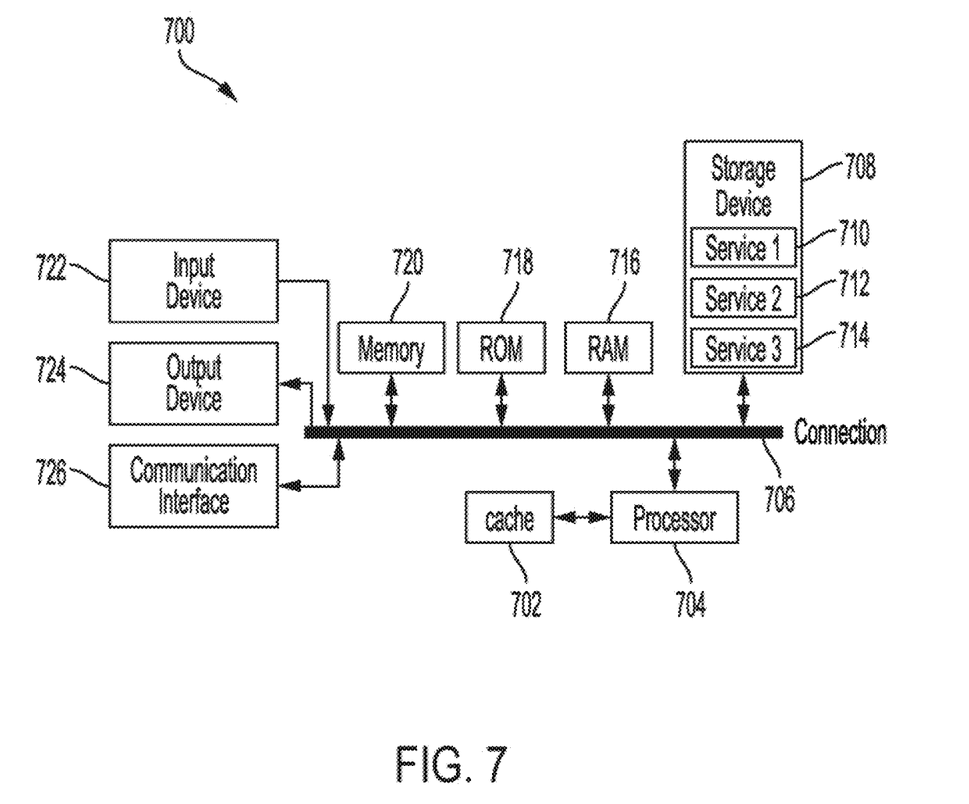
FIG. 7 illustrates an example computing device in accordance with some examples.

FIG. 7 illustrates an example computing system 700 for implementing certain aspects of the present technology. In this example, the components of the system 700 are in electrical communication with each other using a connection 706, such as a bus. The system 700 includes a processing unit (CPU or processor) 704 and a connection 706 that couples various system components including a memory 720, such as read only memory (ROM) 718 and random access memory (RAM) 716, to the processor 704.

The system 700 can include a cache of high-speed memory connected directly with, in close proximity to, or integrated as part of the processor 704. The system 700 can copy data from the memory 720 and/or the storage device 708 to cache 702 for quick access by the processor 704. In this way, the cache can provide a performance boost that avoids processor 704 delays while waiting for data. These and other modules can control or be configured to control the processor 704 to perform various actions. Other memory 720 may be available for use as well. The memory 720 can include multiple different types of memory with different performance characteristics. The processor 704 can include any general purpose processor and a hardware or software service, such as service 1 710, service 2 712, and service 3 714 stored in storage device 708, configured to control the processor 704 as well as a special-purpose processor where software instructions are incorporated into the actual processor design. The processor 704 may be a completely self-contained computing system, containing multiple cores or processors, a bus, memory controller, cache, etc. A multi-core processor may be symmetric or asymmetric.

To enable user interaction with the computing system 700, an input device 722 can represent any number of input mechanisms, such as a microphone for speech, a touch-sensitive screen for gesture or graphical input, keyboard, mouse, motion input, speech and so forth. An output device 724 can also be one or more of a number of output mechanisms known to those of skill in the art. In some instances, multimodal systems can enable a user to provide multiple types of input to communicate with the computing system 700. The communications interface 726 can generally govern and manage the user input and system output. There is no restriction on operating on any particular hardware arrangement and therefore the basic features here may easily be substituted for improved hardware or firmware arrangements as they are developed.

Storage device 708 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 716, read only memory (ROM) 718, and hybrids thereof.

The storage device 708 can include services 710, 712, 714 for controlling the processor 704. Other hardware or software modules are contemplated. The storage device 708 can be connected to the connection 706. In one aspect, a hardware module that performs a particular function can include the software component stored in a computer-readable medium in connection with the necessary hardware components, such as the processor 704, connection 706, output device 724, and so forth, to carry out the function.

It is to be understood that the systems described herein can be implemented in hardware, software, firmware, or combinations of hardware, software and/or firmware. In some examples, image processing may be implemented using a non-transitory computer readable medium storing computer executable instructions that when executed by one or more processors of a computer cause the computer to perform operations. Computer readable media suitable for implementing the control systems described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer readable medium that implements an image processing system described in this specification may be located on a single device or computing platform or may be distributed across multiple devices or computing platforms.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. A method for controlling a left ventricular assist device (LVAD) comprising a pump, comprising:
    obtaining, via a transducer, a precordial sound recording including at least a first sound component corresponding to a heart and a second sound component corresponding to the LVAD;
    filtering, via a processor, at least a portion of the second sound component from the precordial sound recording to yield a filtered precordial sound recording;
    determining, via the processor, based on the filtered precordial sound recording, a presence or absence of at least one acoustic biomarker, the at least one acoustic biomarker comprising a pulse synchronized sound (PSS) acoustic biomarker associated with the LVAD during one or more periodic rotational speed oscillations of the pump;
    adjusting, via the processor, a rotational speed of the pump in response to the at least one acoustic biomarker being absent; and
    repeating the steps of obtaining, filtering, determining, and adjusting until the at least one acoustic biomarker is present.

2. The method of claim 1, wherein the at least one acoustic biomarker comprises one or more peaks in an amplitude of the filtered precordial sound recording.

3. The method of claim 2, wherein the one or more peaks in the amplitude correspond to the one or more periodic rotational speed oscillations of the LVAD.

4. The method of claim 1, wherein obtaining the precordial sound recording comprises:
    processing the precordial sound recording with a band pass filter; and
    reducing a sampling rate of the precordial sound recording.

5. The method of claim 1, wherein determining the at least one acoustic biomarker comprises:
    determining a normalized power spectral density within a frequency range of 20 hertz to 300 hertz.

6. The method of claim 1, further comprising:
    determining, based on the rotational speed of the pump and a number of impeller blades of the pump, a frequency spectrum corresponding to the LVAD, wherein filtering the portion of the second sound component comprises filtering the frequency spectrum corresponding to the LVAD.

7. The method of claim 1, further comprising:
    processing the filtered precordial sound recording to identify one or more stages of a cardiac cycle.

8. The method of claim 1, further comprising:
    in response to determining that the at least one acoustic biomarker is not present, identifying an adjustment of the rotational speed of the LVAD.

9. The method of claim 1, wherein the PSS acoustic biomarker comprises three transient energy bursts in the filtered precordial sound recording having a bandwidth that is wider than sounds associated with the pump.

10. The method of claim 1, wherein determining, based on the filtered precordial sound recording, the presence or absence of the at least one acoustic biomarker comprises:
    detecting the PSS acoustic biomarker using a machine learning classifier.

11. An apparatus comprising:
    a left ventricular assist device (LVAD) comprising a pump;
    at least one memory;
    at least one transducer; and
    at least one processor coupled to the at least one memory and the at least one transducer, the at least one processor configured to:
        obtain, via the at least one transducer, a precordial sound recording including at least a first sound component corresponding to a heart and a second sound component corresponding to the LVAD;
        filter at least a portion of the second sound component corresponding to the LVAD from the precordial sound recording to yield a filtered precordial sound recording;
        determine, based on the filtered precordial sound recording, a presence or absence of at least one acoustic biomarker, the at least one acoustic biomarker comprising a pulse synchronized sound (PSS) acoustic biomarker associated with the LVAD during one or more periodic rotational speed oscillations of the pump;
        adjust a rotational speed of the pump in response to the at least one acoustic biomarker being absent; and
        repeat the steps of obtaining, filtering, determining, and adjusting until the at least one acoustic biomarker is present.

12. The apparatus of claim 11, wherein the at least one acoustic biomarker comprises one or more peaks in an amplitude of the filtered precordial sound recording.

13. The apparatus of claim 12, wherein the one or more peaks in the amplitude correspond to the one or more periodic rotational speed oscillations of the LVAD.

14. The apparatus of claim 11, wherein, to obtain the precordial sound recording, the at least one processor is further configured to:
    process the precordial sound recording with a band pass filter; and
    reduce a sampling rate of the precordial sound recording.

15. The apparatus of claim 11, wherein to determine the at least one acoustic biomarker the at least one processor is further configured to:
    determine a normalized power spectral density within a frequency range of 20 hertz to 300 hertz.

16. The apparatus of claim 11, wherein the at least one processor is further configured to:
    determine, based on the rotational speed of the pump and a number of impeller blades of the pump, a frequency spectrum corresponding to the LVAD, wherein filtering the portion of the second sound component comprises filtering the frequency spectrum corresponding to the LVAD.

17. The apparatus of claim 11, wherein the at least one processor is further configured to:
    process the filtered precordial sound recording to identify one or more stages of a cardiac cycle.

18. The apparatus of claim 11, wherein the at least one processor is further configured to:

in response to a determination that the at least one acoustic biomarker is not present, identify an adjustment of the rotational speed of the LVAD.

19. A non-transitory computer-readable storage medium having stored thereon instructions which, when executed by one or more processors, cause the one or more processors to perform a method for controlling a left ventricular assist device (LVAD) comprising a pump, the method comprising:
  obtaining, via a transducer, a precordial sound recording including at least a first sound component corresponding to a heart and a second sound component corresponding to the LVAD;
  filtering, via the one or more processors, at least a portion of the second sound component from the precordial sound recording to yield a filtered precordial sound recording;
  determining, via the one or more processors, based on the filtered precordial sound recording, a presence or absence of at least one acoustic biomarker, the at least one acoustic biomarker comprising a pulse synchronized sound (PSS) acoustic biomarker associated with the LVAD during one or more periodic rotational speed oscillations of the pump;
  adjusting, via the one or more processors, a rotational speed of the pump in response to the at least one acoustic biomarker being absent; and
  repeating the steps of obtaining, filtering, determining, and adjusting until the at least one acoustic biomarker is present.

20. The non-transitory computer-readable storage medium of claim 19, wherein the at least one acoustic biomarker comprises one or more peaks in an amplitude of the filtered precordial sound recording.

21. The non-transitory computer-readable storage medium of claim 20, wherein the one or more peaks in the amplitude correspond to a periodic speed oscillation of the LVAD.

22. The non-transitory computer-readable storage medium of claim 19, comprising instructions which, when executed by one or more processors, cause the one or more processors to:
  process the filtered precordial sound recording to identify one or more stages of a cardiac cycle.

* * * * *